United States Patent [19]

Hitzman et al.

[11] Patent Number: 5,750,392
[45] Date of Patent: May 12, 1998

[54] COMPOSITION FOR REDUCING THE AMOUNT OF AND PREVENTING THE FORMATION OF HYDROGEN SULFIDE IN AN AQUEOUS SYSTEM, PARTICULARLY IN AN AQUEOUS SYSTEM USED IN OIL FIELD APPLICATIONS

[75] Inventors: Donald O. Hitzman; George T. Sperl; Kenneth A. Sandbeck, all of Bartlesville, Okla.

[73] Assignee: Geo-Microbial Technologies, Inc., Ochelata, Okla.

[21] Appl. No.: 306,324

[22] Filed: Sep. 15, 1994

Related U.S. Application Data

[62] Division of Ser. No. 18,288, Feb. 16, 1993, Pat. No. 5,045, 531.

[51] Int. Cl.$^6$ .............................. C12N 1/00; C12N 1/12; C12N 1/20
[52] U.S. Cl. .................. 435/243; 435/252.1; 435/260
[58] Field of Search .......................... 435/243, 252.1, 435/260

[56] References Cited

U.S. PATENT DOCUMENTS

| | | |
|---|---|---|
| 3,607,736 | 9/1971 | Yusho .......................... 210/11 |
| 4,049,559 | 9/1977 | Grier et al. . |
| 4,161,397 | 7/1979 | Bellet et al. .......................... 435/260 |
| 4,384,956 | 5/1983 | Mulder . |
| 4,415,461 | 11/1983 | Mansel et al. . |
| 4,591,443 | 5/1986 | Brown et al. . |
| 4,620,595 | 11/1986 | Schutt . |
| 4,681,687 | 7/1987 | Mouchè et al. . |
| 4,683,064 | 7/1987 | Hallberg et al. . |
| 4,696,802 | 9/1987 | Bedell . |
| 4,879,240 | 11/1989 | Sublette et al. . |
| 4,880,542 | 11/1989 | Sublette . |
| 4,911,843 | 3/1990 | Hunniford et al. . |
| 5,074,991 | 12/1991 | Weers . |
| 5,141,647 | 8/1992 | Bhadra . |
| 5,250,483 | 10/1993 | Sperl et al. .......................... 502/7 |

FOREIGN PATENT DOCUMENTS

| | | |
|---|---|---|
| 12867 | 5/1996 | WIPO . |

OTHER PUBLICATIONS

Knapp et al., "Microbial Field Pilot Study", 1988, pp. 159–162.
Sperl et al., "The Use of Natural Microflora, Electron Acceptors and Energy Sources for Enhanced Oil Recovery", Abstract.
Knapp et al., Microbially Enhanced Oil Recovery Field Pilot Payne County, Oklahoma, Abstract.
McInerney et al., "Causes and Control of Microbially Induced Souring", Abstract.

*Primary Examiner*—Leon B. Lankford, Jr.
*Attorney, Agent, or Firm*—Foley & Lardner

[57] ABSTRACT

Hydrogen sulfide present in an aqueous system is removed and the production of hydrogen sulfide by sulfate-reducing bacteria (SRB) is eliminated by introducing into the system nitrite and nitrate and/or molybdate ions, whereby denitrifying microorganisms outcompete the sulfate-reducing bacteria for the available carbon nutrients, thus preventing the SRB from producing hydrogen sulfide and the nitrite along with the denitrifying microorganisms remove hydrogen sulfide already present in the system. The system which contains the denitrifying microorganisms and which is essentially free of hydrogen sulfide can enhance oil recovery by means of a microbial enhanced oil recovery mechanisms.

17 Claims, No Drawings

COMPOSITION FOR REDUCING THE AMOUNT OF AND PREVENTING THE FORMATION OF HYDROGEN SULFIDE IN AN AQUEOUS SYSTEM, PARTICULARLY IN AN AQUEOUS SYSTEM USED IN OIL FIELD APPLICATIONS

This application is a division of application Ser. No. 08/018,288, filed Feb. 16, 1993, now U.S. Pat. No. 5,045, 531 issued Apr. 11, 1995.

BACKGROUND OF THE INVENTION

1. Field of the Invention

The invention relates to a method of reducing the amount of hydrogen sulfide in an aqueous system, particularly in an aqueous system used in oil-field applications.

The invention further relates to a method of preventing sulfate-reducing bacteria from forming hydrogen sulfide in an aqueous system.

The invention further relates to a method of using an aqueous system which has a reduced amount of hydrogen sulfide and a reduced tendency to become contaminated with hydrogen sulfide in enhanced oil recovery. The invention also relates to compositions useful in these methods.

2. Background of the Invention

Many oil reserves have turned sour due to the microbial production of hydrogen sulfide ($H_2S$). The hydrogen sulfide is produced by sulfate-reducing bacteria which convert sulfate in the system to sulfide. These bacteria arise during the drilling for oil and may also be indigenously present before the drilling. J. R. Postgate's book "The Sulphate-Reducing Bacteria", second edition, Cambridge University Press 1984, describes these bacteria and their affect on oil fields.

The hydrogen sulfide causes corrosion of the equipment used to recover the oil and can drastically damage the production capabilities of the oil field and also lowers the commercial value of the recovered crude oil. Accordingly, there has been intensive investigation directed at preventing the formation of hydrogen sulfide and/or removing the hydrogen sulfide once it is produced in oil fields.

For example, it is known that the addition of molybdates will inhibit and/or kill the sulfate-reducing bacteria (SRB) which are responsible for the production of hydrogen sulfide in natural environments, such as sediments. However, this method requires that vast amounts of molybdates, e.g., in excess of 3,000 ppm in the water to be treated, be used to effectively control the hydrogen sulfide production by SRB. The use of such large amount of molybdates has the associated disadvantages of high cost due to the limited availability of molybdates and lower efficiency in saline environments or in other brine environments such as connate waters.

Also it is known that the addition of nitrates to a system containing SRB will reduce the amount of SRB in the system and thus the amount of hydrogen sulfide formed by SRB. This method relies on strains of *Thiobacillus denitrificans* which are inhibited by organics which are present in oil field waters.

Accordingly, there is a need to provide an economical and effective means to remove hydrogen sulfide which is present in aqueous systems. There is further a need to prevent the formation of further hydrogen sulfide by sulfate-reducing bacteria which may already be present in the system and/or added later during the use of the system. There is further a need to provide an aqueous system which is useful in the recovery of oil which contains a reduced amount of hydrogen sulfide and furthermore will not be susceptible to forming hydrogen sulfide at a point later in the process, so that the system will not adversely affect the equipment used in the process. These and other needs have been solved by the present invention.

SUMMARY OF THE INVENTION

In accordance with the present invention there is provided a method of reducing the amount of hydrogen sulfide in an aqueous system comprised of water and hydrogen sulfide or preventing the formation of hydrogen sulfide in an aqueous system; comprising the step of bringing nitrate and nitrite ions, or compounds which yield these ions, into contact with the aqueous system in a concentration sufficient to establish and enhance the growth of denitrifying bacteria, wherein denitrifying bacteria are present in the aqueous system prior to the contacting step, and/or added concurrently with or after the ions are brought into contact with the system.

In accordance with another aspect of the present invention there is provided a method of reducing the amount of hydrogen sulfide in an aqueous system comprised of water and hydrogen sulfide or preventing the formation of hydrogen sulfide in an aqueous system, comprising the step of bringing molybdate and nitrite ions or compounds which yield these ions, into contact with an aqueous system containing sulfate-reducing bacteria in a concentration sufficient to inhibit or kill the sulfate-reducing bacteria.

In accordance with another aspect of the present invention there has been provided a method of using the system treated with the nitrite and nitrate and/or molybdate ions in a microbial enhanced oil recovery process comprising the step of injecting the treated aqueous fluid into a subterranean oil-bearing formation to displace oil from the formation. In accordance with other aspects of the invention, there has been provided compositions useful in the above methods, comprising (a) nitrite ions or compounds which yield these ions, and (b) at least one of nitrate and molybdate ions or compounds which yield these ions.

Further objects, features, and advantages of the present invention will become apparent from the detailed description of preferred embodiments which follows.

DETAILED DESCRIPTION OF THE PREFERRED EMBODIMENTS

The present invention can be used anywhere sulfate-reducing bacteria (SRB) are causing or have caused or have the potential for causing hydrogen sulfide generation. The addition of both nitrate and nitrite or of both molybdate and nitrite affects both removal of preformed $H_2S$ and in addition prevents further generation of $H_2S$ by the SRB, which may be present in the system or may be added later, such as during the drilling operation of oil fields.

One application where SRB cause severe problems is in the field of oil recovery. The SRB generate hydrogen sulfide which corrodes the processing equipment and can cause severe damage to the oil-recovery capabilities of the system, and lowers the market value of the oil produced. Accordingly, the present invention is discussed below in the context of oil-recovery. The process of the present invention is not limited to oil-field applications, however, but as noted above, can be used in any application which has as a goal the control of the hydrogen sulfide generation by SRB and/or the goal of removing preformed hydrogen sulfide. For example, the present invention can be used to control hydrogen sulfide in oil storage tanks, oil and gas pipelines, cooling tower water, coal slurry pipelines, and other tanks or equipment that contain water or have a water phase. The treatment can also be used in pits or water containment ponds or in water injection systems where water is put underground.

According to a first embodiment of the present invention, nitrate and nitrite ions are contacted with a system to be treated for removal of hydrogen sulfide and/or prevention of hydrogen sulfide formation by SRB. The addition can be done in any desired manner. For example, the nitrate and nitrite may be prepared as a single aqueous solution or as separate solutions and then added to the system to be treated in either a batch or continuous manner. The method of treatment depends on the system being treated. For example, if a single oil well is to be treated then a single batch injection (although over as much as 3-days) of nitrate and nitrite may be most expedient. If an entire oil-recovery system is to be treated, however, a continuous process may be best.

The important consideration is that enough of the nitrate and nitrite ions are added to deny the SRB the carbon source they need to convert the sulfate to sulfide by encouraging the growth of denitrifying organisms (denitrifiers) so that they will consume the carbon source previously utilized by the SRB. Hence, the amount of nitrate and nitrite added depends on the amount of carbon-source present in the system to be treated. For example, if the water to be treated contains 1000 ppm of acetate which was previously all used by the SRB to convert sulfate to sulfide, enough of the nitrate-nitrite should be added so that the denitrifying microorganisms consume the 1000 ppm of acetate before the SRB. It has been found that about 200 ppm of nitrate and about 100 ppm nitrite accomplishes the desired result.

Upon a reading of the present specification and principles described herein, the ordinary skilled artisan will be able to match the amount of nitrate and nitrite to be added based upon the amount of carbon source present in the system. In general, less than about 3000 ppm of the total of nitrate and nitrite ions are added to the aqueous system. More particularly, between about 25 and about 500 ppm of the total of nitrate and nitrite ions are added to the aqueous system with between about 1 and about 500 parts of nitrite ions are added to the aqueous system and between about 1 and 500 parts of nitrate ions added to the aqueous system. Preferably 10–200 parts of each ion are added. The ratio of nitrate to nitrite ions added is generally between about 50:1 to about 1:50, more particularly from about 1:10 to about 10:1 parts nitrate to nitrite, with a ratio of between about 5:1 to about 1:1 nitrate to nitrite being preferred in oil-field applications.

The nitrate and nitrite may be added to the system in any desired form. For example, the counter-ion is not critical and accordingly any desired form of the nitrate and nitrite may be added so long as the nitrite and nitrate ions will perform their desired function once added to the system. At the present time, adding the ions in the form of their sodium salts has proved advantageous due to economic and availability considerations. But, other counter ions, such as ammonium can be used. Also, compounds which will yield nitrite or nitrate ions once added to an aqueous system can be used.

As alluded to above, the nitrate/nitrite system operates by promoting the growth of denitrifying microorganisms which are usually present in the aqueous system along with the SRB. If these denitrifying microorganisms are not present or not present in an adequate amount, however, they may be added to the system to be treated along with the nitrate/nitrite system.

The denitrifying bacteria compete with the SRB for the carbon-based nutrients which are present in the system or which may be added to the system. That is, both types of microorganisms compete for the same type of nutrients, and due to thermodynamic and physiological considerations, the denitrifying bacteria are much better competitors. Hence, the SRB are left without sufficient carbon source to produce hydrogen sulfide. This lack of carbon nutrient may not kill the SRB directly, but it does not allow for the SRB to produce hydrogen sulfide.

The carbon nutrients added are generally acetate and it may be indigenously present in the system to be treated or added before and/or during the treatment. Since SRB generally require carbon nutrients to grow and produce the hydrogen sulfide, if the system contains SRB which are currently generating hydrogen sulfide, the system will generally contain the necessary carbon nutrients for the growth of the denitrifiers. Hence, generally, it is not necessary to add additional carbon nutrients if there are presently active SRB in the system which are producing the sulfide.

But, if the hydrogen sulfide problem is not caused by current SRB activity, for example, the hydrogen sulfide was preformed in the past by SRB's, and there is not sufficient carbon nutrients in the system, then a carbon source would have to be added to grow the denitrifiers.

Similarly, if the system does not currently contain SRB which are generating hydrogen sulfide, but there is the potential that the system may in the future contain SRB, then a prophylactic treatment with nitrate/nitrite and if need be a denitrifier would preclude future SRB activity. In this case, a carbon source may be added along with the denitrifiers so as to encourage the growth of the denitrifiers, thus preventing any SRB which may arise in the future from producing hydrogen sulfide, due to the consumption of available nutrients by the denitrifiers, leaving none for the SRB.

Accordingly, the present invention can be used to treat a system which contains SRB which are producing hydrogen sulfide, or a system containing hydrogen sulfide due to the presence of SRB in the past, or to treat a system which may contain SRB in the future. The presence of the denitrifiers and nitrate and nitrite ions will remove any preformed hydrogen sulfide and prevent its formation in the future by SRB.

The carbon sources that are present in the system and/or that can be added if need be, in addition to or in place of acetates, include any known carbon nutrients for denitrifiers. For example, simple carbon/hydrogen compounds such as Krebs cycle intermediates, malonate, citrates, lactates, ethanol, glycerol and the like can be used as nutrients to grow the denitrifying organisms. Most oil-fields indigenously contain the necessary carbon sources to grow the denitrifying bacteria. Also, during production and operation of the oil field, compounds which serve as nutrients are often added. However, additional carbon sources, along with other desired nutrients, such as phosphate salts, for the denitrifying organisms can be added, so as to obtain a nutritional balance which encourages the establishment and growth of the denitrifying organisms.

The denitrifying organisms use the carbon nutrient, which is generally indigenous to the system, but can be added, such as acetate, along with the added nitrates to grow. The nitrite is added because it helps in a thermodynamic manner the growth of the denitrifiers and thus the denitrifiers' consumption of the carbon source. Also, the nitrites react with the preformed hydrogen sulfide made by the SRB, thus immediately lowering the preformed sulfide. The nitrite also acts to inhibit the actions of the SRB in their further production of hydrogen sulfide.

The denitrifying organisms are bacteria and, if the system is one used in oil field applications, are usually indigenous in the system to be treated. If not already present, the denitrifiers can be added before, after or concomitant with the addition of the nitrite and nitrate ions. They may be added in a batch manner or in a continuous process. Denitrifiers are known to those skilled in the art and are described, for example in "The Prokaryotes: A Handbook on Habitats, Isolation, and Identification of Bacteria", Volumes 1–4 (Springer-Verlag, 1981). These bacteria utilize nitrate or nitrite as a terminal electron acceptor, i.e., gain energy by respiring it as animals do with oxygen. Some of the bacteria convert the nitrate ($NO_3$) to $N_2$, while others convert it to $NH_3$. Denitrifiers can grow on the same carbon/energy source which the SRB utilize and as noted previously, denitrifiers compete more effectively for the carbon/energy sources, thus denying their use for SRB growth and subsequent sulfide formation.

The action of the nitrite and nitrate is unexpectedly synergistic. That is, by adding both together, less of both are needed to accomplish the removal of the $H_2S$ and prevention of further $H_2S$ generation by SRB. As previously noted, the appropriate amount of ions added depends on the parameters of the system to be treated, including carbon levels, hydrogen sulfide level, current SRB level, and the like. Those skilled in the art using the principles described in this application can determine the appropriate amount of ions to be added taking into consideration that the system should allow the denitrifiers to use up the available carbon sources so as to prevent SRB from producing hydrogen sulfide and also so as to remove any preformed hydrogen sulfide.

A further advantage of growing the denitrifiers, is that when they grow they will use hydrogen sulfide which remains in the system, i.e., not removed by interaction with the nitrite, as a nutrient. This effect further lowers the amount of hydrogen sulfide in the system and the associated undesired results.

Furthermore, the denitrifying microorganisms will act as agents which will help in the release of oil by the known mechanism known to release oil including water diversion, biopolymer and biosurfactant production, $N_2$ formation, gas production, pH change, and the like during microbial enhanced oil recovery processes (MEOR). That is, the denitrifying bacteria and products of such bacteria cause the release of oil by the above noted mechanisms, whereby water diversion occurs in the high permeability zones directing the water to be preferentially diverted into lower permeability zones, causing the enhanced displacement of oil.

Hence, growing the denitrifiers in an aqueous system not only removes hydrogen sulfide and prevents the formation of hydrogen sulfide, but also results in an aqueous system which can be used in MEOR processes. The aqueous system is treated with the nitrite and nitrate ions either before or during the oil-recovering steps so that hydrogen sulfide does not enter the subterranean formation. The system of the present invention may then be used in enhanced oil recovery processes which are known per se. For example, the treated system is injected into a subterranean oil-bearing formation to displace oil from the formation.

The system containing denitrifiers with reduced or no hydrogen sulfide is more effective in recovering oil because the oil does not become sour and there is less corrosion which increases the expense of the operation and ultimately the abandonment of oil-fields. Furthermore, since there is less or no hydrogen sulfide, iron sulfide is not produced by the reaction of hydrogen sulfide with iron. Iron sulfide is undesirable in oil-fields because it acts as a plugging agent.

In an additional enhancement of the first embodiment of the invention, molybdates are added in combination with the nitrite and nitrate. The molybdate serves to kill or inhibit the SRB. However, the molybdates are added in such an amount so as not to kill or inhibit the denitrifying bacteria. Also, when used in combination with the nitrite and nitrate, much less molybdate is required to obtain the desired inhibition of SRB, than in the known process of using molybdates alone to kill and/or inhibit the SRB.

Hence, the combination of nitrate, nitrite, and molybdate provides advantages over the known use of molybdate alone. In particular, vast amounts of molybdate are needed if used alone, such as greater than 3000 ppm, whereas only about 1 to about 200 ppm, preferably about 5 to about 100 ppm of molybdate are needed when used in combination with the nitrate and nitrite ions. The molybdate to be added can be in the form of any molybdate salt or compound which yields molybdate ions. Currently sodium and lithium molybdate are used due to economic and availability considerations.

In accordance with a second embodiment, the present inventors have found that instead of using nitrite and nitrate ions with the optional use of molybdate, that a treatment using nitrite and molybdate, without the requirement for using a nitrate, is effective at removing hydrogen sulfide from an aqueous system and/or preventing the future formation of hydrogen sulfide by SRB.

The second embodiment is analogous to the first embodiment except that the nitrate need not be added. The addition of nitrate ions is not required in this embodiment because denitrifiers can grow on either nitrate or nitrite. Accordingly, enough nitrite is added to enhance the growth of the denitrifiers. This is usually at least 1 ppm of nitrite up to about 500 ppm of the nitrite. The person skilled in the art based on the principles of the present invention will be able to determine based on the nutrient and ion content of the aqueous system to be treated how much nitrite should be added to enhance the growth of the denitrifiers.

As previously noted, the nitrite also reacts with preformed hydrogen sulfide immediately lowering the amount of the sulfide. Accordingly, the amount of added nitrite is also a function of the amount of preformed hydrogen sulfide in the system to be treated.

As in the first embodiment, an important feature is that the growth of the denitrifiers is encouraged. This growth is encouraged by the nitrite ions and the carbon source and other nutrients added or indigenous to the system. Once the denitrifiers are present, they outcompete the SRB for the carbon nutrients, preventing the formation of hydrogen sulfide by the SRB.

As in the first embodiment, the denitrifiers may be already present in the system to be treated and/or added, and the carbon source may be added or be indigenous to the system. Furthermore, the nitrite and molybdate may be added to the system to be treated in any desired chemical form in a batch or continuous manner.

The molybdate is added in an amount sufficient to kill or inhibit the SRB, but so as to not adversely affect the denitrifiers. This amount is generally as in the first embodiment, namely about 1 to about 200 ppm, preferably about 5 to about 100 ppm.

The nitrite and molybdate ions may be used to treat a system which contains active SRB producing hydrogen sulfide or which may contain SRB in the future, or to treat a system containing hydrogen sulfide to effect the removal of the hydrogen sulfide. The treated system can be used in the recovery of oil as can the system treated in the first embodiment.

The action of the nitrite and molybdate ions is unexpectedly synergistic, requiring less of each to be used to inhibit the formation of hydrogen sulfide and remove any hydrogen sulfide already present, then if either were used alone.

The present invention is demonstrated by the following Example, but it is to be understood that the Example is for exemplary purposes only and does not serve to limit the invention.

EXAMPLE

The data in the table below was generated by laboratory bottle tests. A series of sterile synthetic SRB growth medium bottles were inoculated with a constant number of microorganisms containing both constant numbers of SRB and denitrifiers. Different bottles (samples) were amended to contain varying concentrations of chemical compounds to be tested. SRB growth was judged by sulfide formation; that is lack of SRB growth was judged by the lack of sulfide formation. The results are shown in the table below.

| | ppm ion | | | |
|---|---|---|---|---|
| Sample | nitrate | nitrite | molybdate | SRB Growth |
| 1 | 200 | | | Yes |
| 2 | 100 | | | Yes |
| 3 | | 200 | | Yes |
| 4 | | 100 | | Yes |
| 5 | 100 | 100 | | No |
| 6 | 50 | 50 | | No |
| 7 | 1 | | 12 | Yes |
| 8 | 50 | 1 | 12 | No |
| 9 | | 5 | 12 | No |
| 10 | | 50 | 12 | No |
| 11 | 50 | 50 | 12 | No |

Samples 1–4 are comparative examples. As can be seen from these examples, the addition of nitrate or nitrite alone in amounts of 100 or 200 ppm did not prevent the growth of SRB.

Samples 5, 6, 8 and 11 are within the first embodiment of the present invention. As is seen, using both the nitrite and nitrate, even in a reduced amount of 100 parts each or 50 parts each prevented SRB growth. Such results would not have been expected based on the results achieved with nitrate and nitrite alone.

Examples 7 is a comparative example using nitrate and molybdate. This combination did not prevent SRB growth. However, as seen in Examples 9–10 which are within the scope of the second embodiment of the present invention, using a combination of molybdate and nitrite was effective in preventing the growth of SRB.

What is claimed is:

1. A composition useful for synergistically reducing the amount of hydrogen sulfide which may be present in an aqueous system and preventing the formation of hydrogen sulfide in the aqueous system, comprising (a) nitrite ions or compounds which yield these ions, and (b) nitrate ions or compounds which yield these ions, wherein the ions are present in a concentration sufficient to support and enhance the growth of denitrifying bacteria when added to the aqueous systems and in a concentration sufficient to inhibit the growth of sulfate reducing bacteria when added to the aqueous system and wherein the ratio of nitrite to nitrate ions is between about 50:1 to 1:50, and wherein the nitrite and nitrate ions are present in an amount to synergistically reduce the amount of the hydrogen sulfide which may be present in the acrueous system and prevent the formation of hydrogen sulfide in the acrueous system.

2. A composition of claim 1, which comprises each of nitrite, nitrate, and molybdate ions or compounds which yield these ions.

3. A composition of claim 2, wherein the composition is an aqueous solution of the ions.

4. A composition of claim 3, wherein the composition further comprises a carbon source.

5. A composition of claim 3, which consists essentially of sodium nitrite, sodium nitrate, and sodium molybdate.

6. A composition of claim 1, wherein (b) comprises molybdate ions or compounds which yield molybdate ions.

7. A composition of claim 1, which further comprises denitrifying microorganisms.

8. A composition of claim 4, wherein the carbon source comprises an acetate.

9. A composition of claim 1, wherein the composition is an aqueous solution of the ions.

10. A composition of claim 1, wherein the composition further comprises a carbon source.

11. A composition of claim 1, wherein the ratio of nitrate to nitrite ions is between about 1:10 to about 10:1.

12. A composition of claim 1, wherein the ratio of nitrate to nitrite ions is between about 5:1 to about 1:1.

13. A composition of claim 1, wherein the ions are present in a quantity such that the aqueous system to which they are added will contain about 1 to about 500 ppm of nitrate ions and about 1 to about 500 ppm of nitrite ions.

14. A composition of claim 1, wherein the ions are present in a quantity such that the aqueous system to which they are added will contain about 5 to 250 ppm of molybdate ions.

15. A composition of claim 1, wherein nitrate and nitrite ions are present in a quantity such that the aqueous system to which they are added will contain about 25 to 500 ppm of the total of nitrate and nitrite ions.

16. A composition of claim 1, which consists essentially of nitrite ions or compounds which yield these ions, and nitrate ions or compounds which yield these ions.

17. A composition of claim 1, which consists essentially of nitrite ions or compounds which yield these ions, nitrate ions or compounds which yield these ions, and molybdate ions or compounds which yield these ions.

* * * * *